(12) United States Patent
Sherrod et al.

(10) Patent No.: US 6,738,735 B1
(45) Date of Patent: May 18, 2004

(54) METHOD OF DETERMINING THE EFFICIENCY OF AN ABSORBENT ARTICLE HAVING TWO ABSORBENT LAYERS THAT EACH CONTAIN A SUPERABSORBENT

(75) Inventors: Earle Harry Sherrod, Appleton, WI (US); Kuo-Shu Edward Chang, Charlotte, NC (US); Billie Jean Matthews, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 920 days.

(21) Appl. No.: 09/611,822

(22) Filed: Jul. 7, 2000

(51) Int. Cl.$^7$ ............................................. G06F 17/50
(52) U.S. Cl. .................................... 703/2; 604/378
(58) Field of Search .................... 703/2, 6; 604/361, 604/368, 378, 381; 428/218; 442/239

(56) References Cited

U.S. PATENT DOCUMENTS

| 4,673,402 A | 6/1987 | Weisman et al. ............ 604/368 |
| 4,699,619 A | 10/1987 | Bernardin ................... 604/378 |

(List continued on next page.)

FOREIGN PATENT DOCUMENTS

EP 0 695 541 A1 2/1996

OTHER PUBLICATIONS

Yokura et al., H. Objective Hand Measurement of Materials Used for Disposable Diapers, International Journal of Clothing Science and Technology, Bradford: 2000, vol. 12, Iss. 3, p. 184.*

Funk, R., BASF: Keeping Baby Bottoms Dry, M2 Presswire, Coventry: May 3, 2001, p. 1.*

*Primary Examiner*—Russell Frejd
(74) *Attorney, Agent, or Firm*—Thomas J. Connelly

(57) ABSTRACT

A method is disclosed for determining the efficiency of an absorbent article having first and second absorbent layers. The method comprises the steps of selecting a density for the first absorbent layer and for the second absorbent layer. A basis weight for each of the first and second absorbent layers is selected which is at least about 100 grams per square meter. A desired percentage of a superabsorbent to be present in each of the first and second absorbent layers is also selected. The percentage of a superabsorbent present in the first absorbent layer is greater than the percentage of a superabsorbent present in the second absorbent layer. The selected densities and percentages of a superabsorbent are then inserted into the following formula:

$$V \leq [(100 - \% \text{ SAM2}) \times (d2 - d1)] + [(\% \text{ SAM1} - \% \text{ SAM2}) \times d2)]$$

In this formula:

- % SAM1 is the percentage of a superabsorbent present in the first absorbent layer;
- % SAM2 is the percentage of a superabsorbent present in the second absorbent layer;
- d1 is the density of the first absorbent layer expressed in gsm;
- d2 is the density of the second absorbent layer expressed in gsm; and
- V is the desired value to form an efficiency absorbent article.

The selected densities and the selected percentages of a superabsorbent in the first and second absorbent layers are then adjusted to obtain a value "V" which is at least equal to 2.

20 Claims, 2 Drawing Sheets

U.S. PATENT DOCUMENTS

| | | | |
|---|---|---|---|
| 4,842,594 A | 6/1989 | Ness | 604/368 |
| 4,880,419 A | 11/1989 | Ness | 604/368 |
| 4,935,022 A | 6/1990 | Lash et al. | 604/368 |
| 4,994,037 A | 2/1991 | Bernardin | 604/368 |
| 5,188,624 A | 2/1993 | Young, Sr. et al. | 604/378 |
| 5,217,445 A | 6/1993 | Young et al. | 604/381 |
| 5,219,341 A | 6/1993 | Serbiak et al. | 604/361 |
| 5,281,207 A | 1/1994 | Chmielewski et al. | 604/378 |
| 5,294,478 A | 3/1994 | Wanek et al. | 428/218 |
| 5,304,161 A | 4/1994 | Noel et al. | 604/378 |
| 5,348,547 A | 9/1994 | Payne et al. | 604/378 |
| 5,356,403 A | 10/1994 | Faulks et al. | 604/378 |
| 5,368,926 A | 11/1994 | Thompson et al. | 442/239 |
| 5,439,458 A | 8/1995 | Noel et al. | 604/378 |
| 5,454,800 A | 10/1995 | Hirt et al. | 604/378 |
| 5,460,622 A | 10/1995 | Dragoo et al. | 604/378 |
| 5,486,167 A | 1/1996 | Dragoo et al. | 604/384 |
| 5,505,719 A | 4/1996 | Cohen et al. | 604/372 |
| 5,525,407 A | 6/1996 | Yang | 428/218 |
| 5,569,226 A | 10/1996 | Cohen et al. | 604/378 |
| 5,669,894 A | 9/1997 | Goldman et al. | 604/368 |
| 5,728,083 A | 3/1998 | Cohen et al. | 604/368 |
| 5,728,084 A | 3/1998 | Palumbo et al. | 604/378 |
| 5,762,641 A | 6/1998 | Bewick-Sonntag et al. | 604/378 |
| 5,797,894 A | 8/1998 | Cadieux et al. | 604/378 |

* cited by examiner

METHOD OF DETERMINING THE EFFICIENCY OF AN ABSORBENT ARTICLE HAVING TWO ABSORBENT LAYERS THAT EACH CONTAIN A SUPERABSORBENT

FIELD OF THE INVENTION

This invention relates to a method of determining the efficiency of an absorbent article having two absorbent layers that have a selected density, basis weight and each layer contains a superabsorbent. More specifically, this invention relates to a method of determining, without bench testing, the efficiency of a disposable absorbent article having two absorbent layers made from a wettable, fibrous material, each layer having a selected density, basis weight and a desired percentage of a superabsorbent.

BACKGROUND OF THE INVENTION

Many absorbent articles, especially disposable absorbent articles, like diapers, training pants, sanitary napkins, incontinence garments, and the like are constructed with two absorbent layers. Typically, the upper absorbent layer functions as a fluid intake layer and the lower absorbent layer functions as a fluid storage or reservoir layer. Normally, the superabsorbent material is present in the lower absorbent layer. This design allows the fluid which contacts the article to move downward through the upper absorbent and into the lower absorbent layer without being impeded. It is also common practice to construct the upper absorbent layer such that it has a lower density than the lower absorbent layer. This density gradient further facilitates downward fluid movement into the lower absorbent layer.

Now, a method has been invented that can be used to determine the efficiency of an absorbent article having two absorbent layers before the absorbent article is actually manufactured. The absorbent article is constructed from a wettable, fibrous material such as cellulose fluff. The absorbent article has two absorbent layers each having a selected density, basis weight and a desired percentage of a superabsorbent in each of the two layers.

SUMMARY OF THE INVENTION

Briefly, this invention relates to a method of determining the efficiency of an absorbent article having first and second absorbent layers each having a selected density, basis weight and a desired percentage of a superabsorbent. The method includes the steps of selecting a density for the first and second absorbent layers. A basis weight of at least 100 grams per square meter (gsm) is then selected for each of the first and second absorbent layers. The percentages of a superabsorbent present in each of the first and second absorbent layers are also selected such that the percentage of a superabsorbent in the first absorbent layer is greater than the percentage of a superabsorbent in the second absorbent layer. The selected densities and percentages of the superabsorbents are then inserted into the following formula:

$$V \leq [(100 - \% \ SAM2) \times (d2 - d1)] + [(\% \ SAM1 - \% \ SAM2) \times d2]$$

where: % SAM1 is the percentage of a superabsorbent in the first absorbent layer;

%SAM2 is the percentage of a superabsorbent in the second absorbent layer;

d1 is the density of the first absorbent layer expressed in grams per cubic centimeters;

d2 is the density of the second absorbent layer expressed in grams per cubic centimeters; and V is the desired value to form an efficient absorbent article.

The selected densities and the selected percentages of a superabsorbent in the first and second absorbent layers are then adjusted to obtain a value "V" that is at least equal to 2.

The general object of this invention is to provide a method of determining the efficiency, without bench testing, of an absorbent article having two absorbent layers each having a selected density, basis weight and each containing a desired percentage of a superabsorbent. More specifically, this invention relates to a method of determining the efficiency of a disposable absorbent article having two absorbent layers formed from a wettable, fibrous material, such as cellulose fluff and each absorbent layer having a selected density, basis weight and containing a desired percentage of a superabsorbent.

Another object of this invention is to provide a method of determining the makeup of a dual layer absorbent article using a mathematical formula.

A further object of this invention is to provide a method of determining the percentages of a superabsorbent needed to be inserted into each absorbent layer of a two layer absorbent article.

Still another object of this invention is to provide a method of economically designing a two layer absorbent article.

Still further, an object of this invention is to provide an accurate and inexpensive method of designing a two layer absorbent article wherein each layer has a selected density, basis weight and a desired percentage of a superabsorbent.

Other objects and advantages of the present invention will become more apparent to those skilled in the art in view of the following description and the accompanying drawings.

DETAILED DESCRIPTION OF THE PREFERRED EMBODIMENTS

Figure 1:
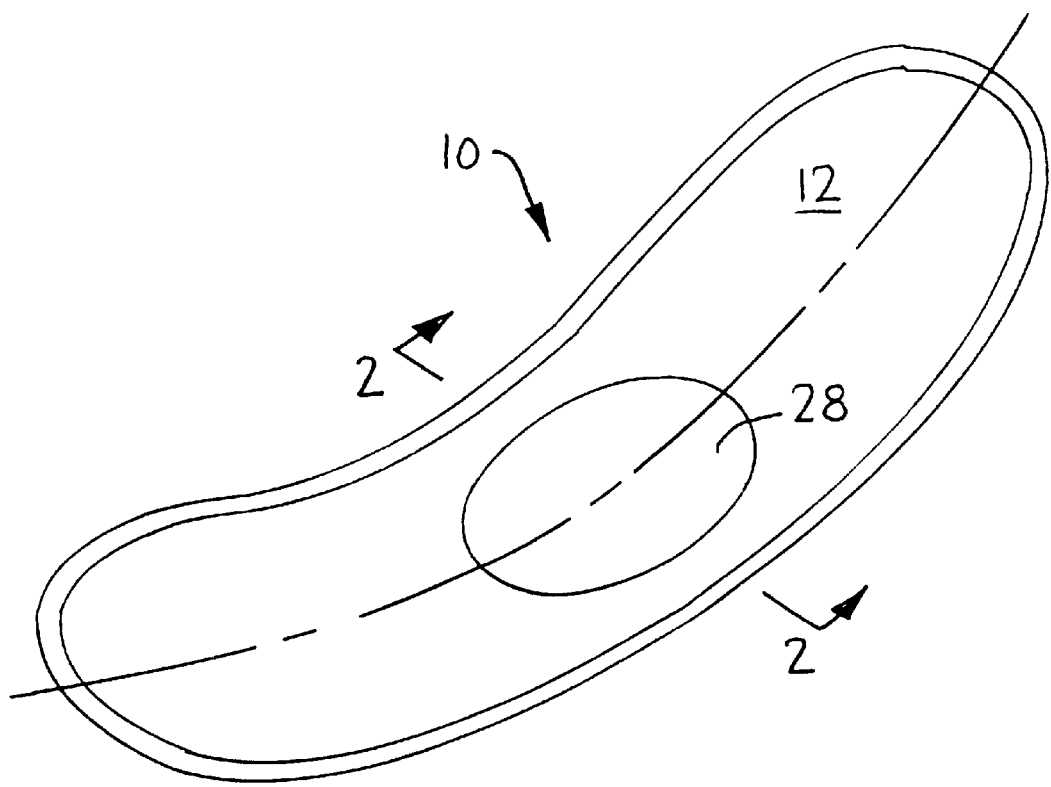
FIG. 1 is a perspective view of an absorbent article in the form of an incontinent pad having two absorbent layers each containing a superabsorbent.
Figure 2:
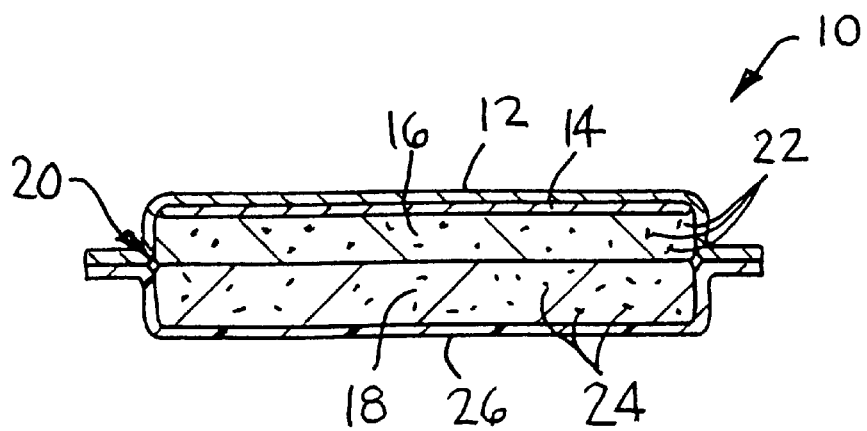
FIG. 2 is a cross-sectional view of the absorbent article shown in FIG. 1 taken along line 2—2.

Referring to FIGS. 1 and 2, an absorbent article 10 is depicted. The absorbent article 10 could be a disposable absorbent article such as a diaper, a sanitary napkin, a pantyliner, an incontinence pad, an incontinence garment, an incontinence brief, an incontinence undergarment, a training pant, etc. The absorbent article 10 could also be a reusable absorbent article or an absorbent article utilizing a disposable insert.

The absorbent article 10 is constructed of multiple layers. Starting from the top, which is the layer that would contact the body of a user, the absorbent article 10 includes a cover 12. The cover 12, also referred to as a bodyside liner, should be liquid-permeable so as to allow body fluids to easily pass therethrough. The most common body fluid that will be encountered by the absorbent article 10 is urine. However, the cover 12 can be designed to allow other body fluids, such as blood and menstrual fluids to readily pass through. The liquid-permeable cover 12 can be constructed from natural and/or synthetic materials. Suitable materials for the cover 12 include those materials that have a soft hand and are pliable. Spunbond is one such material that works extremely well. Spunbond is manufactured and commercially sold by Kimberly-Clark Corporation, having an office at 401 North Lake Street, Neenah, Wis. 54956.

The cover 12 could also be made out of other materials, such as bonded-carded webs, polyolefin, polyester, polypropylene, polyethylene, nylon or other fibrous materials. Specific polyolefins, such as linear low-density polypropylene, linear low-density polyethylene, finely perforated film webs and net materials can also be used. If a thermoplastic film is used, it will be necessary to aperture, perforate or slit it to make it liquid permeable.

Referring to FIG. 2, a surge or transfer layer 14 is depicted positioned below the cover 12. A surge layer rapidly intakes and/or draws liquid in, spreads the liquid out in the x-y directions and can serve as a temporary reservoir until the liquid can be transferred to the underlying absorbent 16. A transfer layer draws liquid in and facilitates rapid transfer of the liquid to the underlying absorbent 16. The surge or transfer layer 14 does not have to be present but if used, should function to draw body fluid which is deposited on the cover 12 down into the absorbent article 10. The surge or transfer layer 14 can be constructed of any commonly available surge or transfer materials. Typical surge and/or transfer materials include spunbond, bonded-carded webs, meltblown and meltspun. Spunbond and meltspun are materials manufactured by Kimberly-Clark Corporation, having an office at 401 North Lake Street, Neenah, Wis. 54956.

Preferably, the surge or transfer layer 14 will be in direct contact with the lower surface of the cover 12 so as to facilitate the downward movement of the body fluid away from the cover 12. By quickly directing the body fluid down into the absorbent article 10, the cover 12 will maintain a dry feel against the user's skin and rewetting problems can be minimized or eliminated. Rewetting is a phenomenon that occurs when body fluid previously absorbed by the absorbent article 10 is pushed back towards the cover 12 as the absorbent article 10 is squeezed or compressed by certain movement of the wearer. For example, when a wearer sits down and compresses the absorbent article 10, there is a tendency for the body fluid being retained in the absorbent article to move upward back toward the cover 12. Rewetting is an undesirable feature that should be avoided if possible.

Positioned below the surge or transfer layer 14 is a first absorbent layer 16 and a second absorbent layer 18. The first absorbent layer 16 is located immediately below the surge or transfer layer 14 and is positioned immediately above the second absorbent layer 18. If no surge or transfer layer 14 is present, the first absorbent layer 16 should be in direct contact with the underside of the liquid-permeable cover 12. The first and second absorbent layers, 16 and 18 respectively, should be formed from a wettable, fibrous material. Preferably, the fibrous material is formed from natural fibers. Natural fibers include cellulose fibers such as wood pulp, cellulose fluff, eucalyptus, cotton or regenerated cellulose, as well as fibers from various plants. Each of the first and second absorbent layers, 16 and 18 respectively, can be constructed from a single fibrous material or a combination of two or more different fibrous materials. The fibers can be chemically treated, such as with a surfactant, so as to increase their wettability, if desired. The fibers can also be long, continuous fibers or short, discrete fibers. The fibers can also be non-cellulose fibers formed from polyester, polyolefins, nylons, etc. The first and second absorbent layers, 16 and 18 respectively, should be homogeneous mixtures of the fibrous material(s).

It should be noted that the lateral and longitudinal extent of the first and second absorbent layers, 16 and 18 respectively, could be selected to provide good utilization and perception of dryness. Either absorbent layer 16 or 18 can be made longer and/or wider relative to the other absorbent layer. In addition, the first absorbent layer 16 can be offset from the second absorbent layer 18 in order to achieve the desired performance.

The density "d1" of the first absorbent layer 16 can be equal to or greater than about 0.08 grams per cubic centimeter (g/cc). Preferably, the density "d1" of the first absorbent layer 16 should range from between about 0.08 g/cc to about 0.18 g/cc. Most preferably, the density "d1" of the first absorbent layer 16 should range from between about 0.10 g/cc to about 0.15 g/cc. The density "d1" of the first absorbent layer 16 is important for it allows the first layer 16 to maintain an open structure even when the superabsorbent present in this layer starts to swell. The density "d1" of the first absorbent layer 16 should be selected so as to ensure rapid movement of the incoming body fluid down into the second absorbent layer 18.

The density "d2" of the second absorbent layer 18 can be equal to or greater than about 0.08 g/cc. Preferably, the density "d2" of the second absorbent layer 18 should range from between about 0.1 g/cc to about 0.2 g/cc. Most preferably, the density "d2" of the second absorbent layer 18 should range from between about 0.12 g/cc to about 0.17 g/cc. Contrary to popular belief that the lower absorbent layer must have a higher density than the other absorbent layers, we have found that the density "d2" of the second absorbent layer 18 can be selected such that it is less than, equal to or greater than the density "d1" of the first absorbent layer 16 so long as the value, V is greater than or equal two. In addition, the density "d2" of the second absorbent layer 18 should be selected to assure adequate wicking of the body fluid within the second absorbent layer 18. Good wicking characteristics provide a means for directing the body fluid outward in the longitudinal and transverse directions away from the location where the body fluid contacts the second absorbent layer 18.

When the absorbent article 10 is a disposable absorbent article designed to absorb human body fluids, it is advantageous to construct the first and second absorbent layers, 16 and 18 respectively, such that each has a basis weight of at least about 100 grams square meter (gsm). Preferably, each absorbent layer 16 and 18 has a basis weight of at least about 150 gsm, and most preferably, each absorbent layer 16 and 18 has a basis weight of at least about 200 gsm.

The upper limit of the basis weight for each of the absorbent layers 16 and 18 can vary depending on the kind of article produced, as well as on the size, shape, thickness and configuration of the absorbent article. For example, when the absorbent article 10 is designed as an incontinence pad, it may have a narrower width in the crotch section than if it were a diaper. Also, an absorbent article design to be worn by an adult will need a different basis weight than an absorbent article designed to be worn by an infant or child. A good criteria for selecting an upper limit for the basis weight of the first absorbent layer 16 is to select a value which is less than or equal to about 200 times the width of the first absorbent layer 16. In selecting this basis weight value, the width of the first absorbent layer 16 is measured in centimeters (cm) at the narrowest point along its length. Preferably, the upper limit of the basis weight for the first absorbent layer 16 is less than or equal to about 150 times the width of the first absorbent layer 16, measured in centimeters (cm) at the narrowest point along its length.

Most preferably, the upper limit of the basis weight for the first absorbent layer 16 is less than or equal to about 120 times the width of the first absorbent layer 16, measured in centimeters (cm) at the narrowest point along its length.

A good criteria for selecting an upper limit of the basis weight for the second absorbent layer 18 is to select a value which is less than or equal to about 200 times the width of the second absorbent layer 18. In selecting this basis weight value, the width of the second layer 18 is measured in centimeters (cm) at the narrowest point along its length. Preferably, the upper limit of the basis weight for the second absorbent layer 18 is less than or equal to about 150 times the width of the second absorbent layer 18, measured in centimeters (cm) at the narrowest point along its length. Most preferably, the upper limit of the basis weight for the second absorbent layer 18 is less than or equal to about 100 times the width of the second absorbent layer 18, measured in centimeters (cm) at the narrowest point along its length.

It should be noted that the narrowest width of each of the first and second absorbent layers, 16 and 18 respectively, could be the same or be a different dimension.

Another way of determining an adequate basis weight for each of the first and second absorbent layers, 16 and 18 respectively, is to add up the basis weight in the two absorbent layers 16 and 18. The two absorbent layers 16 and 18 together form an absorbent core 20. The total or combined basis weight for the absorbent core 20 should be equal to or greater than about 200 gsm. Preferably, the basis weight of the absorbent core 20 should be equal to or greater than about 300 gsm. Most preferably, the basis weight of the absorbent core 20 should be equal to or greater than about 400 gsm.

The basis weight of the absorbent core 20 can also be expressed in relation to its width along the length of the absorbent article 10. The basis weight of the absorbent core 20 should be less than about 300 times the width of the absorbent core 20, measured in centimeters (cm) at the narrowest point along the length of the absorbent article 10. Preferably, the basis weight of the absorbent core 20 should be less than about 225 times the width of the absorbent core 20, measured in centimeters (cm) at the narrowest point along the length of the absorbent article 10. Most preferably, the basis weight of the absorbent core 20 should be less than about 200 times the width of the absorbent core 20, measured in centimeters (cm) at the narrowest point along the length of the absorbent article 10. It should be noted that the width of the absorbent core 20 at its narrowest point should represent that portion of the absorbent core 20 which would be positioned at or near the location where the body fluid would normally contact the absorbent article 10.

Each of the first and second absorbent layers, 16 and 18 respectively, also contains a superabsorbent, 22 and 24 respectively. Each superabsorbent 22 and 24 is also referred to as a superabsorbent material (SAM). The first absorbent layer 16 will contain the superabsorbent 22, also referred to herein as SAM 1, and the second absorbent layer 18 will contain the superabsorbent 24, also referred to herein as SAM2. The superabsorbents 22 and 24 can be identical in composition, size and/or shape or they can be different in one or more attributes. Each of the superabsorbents 22 and 24 can be a hydrocolloidal material that functions to increase the amount of body fluid that the first and second absorbent layers, 16 and 18 respectively, can absorb and/or retain. The superabsorbents 22 and 24 can also increase the fluid retention capabilities of the first and second absorbent layers, 16 and 18 respectively.

The superabsorbents 22 and 24 can be individual particles that are dispersed throughout the entire fibrous structure of the first and second absorbent layers, 16 and 18 respectively. Alternatively, the superabsorbents 22 and 24 can be dispersed into one or more pre-selected areas or regions of each of the first and second absorbent layers, 16 and 18 respectively. The exact positioning of the superabsorbents 22 and 24 will be dependent on the type of absorbent article being produced, the size and shape of the article, as well as the gender of the user of the article. Other factors can also impact the exact placement of the superabsorbents 22 and 24 in the first and second absorbent layers, 16 and 18 respectively. Furthermore, the superabsorbents 22 and 24 can be concentrated in one region versus being evenly dispersed throughout the entire volume of each absorbent layer 16 and 18, if desired. Each of the superabsorbents 22 and 24 can also be formed as a laminate having a superabsorbent material incorporated onto a carrier sheet. The superabsorbents 22 and 24 can be particles of different mesh size and/or shape, or they can be formed as flakes or some other configuration. Preferably, the superabsorbents 22 and 24 are in particle form.

The percentage of superabsorbent 22 dispersed or contained in the first absorbent layer 16 should be in the range of from between about 35% to about 80%. Preferably, the percentage of superabsorbent 22 contained in the first absorbent layer 16 will range from between about 35% to about 65%. Most preferably, the percentage of superabsorbent 22 contained in the first absorbent layer 16 will range from between about 40% to about 60%.

The percentage of superabsorbent 24 dispersed or contained in the second absorbent layer 18 should be less than the percentage of superabsorbent 22 present in the first absorbent layer 16. The reason for this is that the first absorbent layer 16 serves as the major storage layer while the second absorbent layer 16 serves to distribute or wick the liquid longitudinally and transversely. The percentage of superabsorbent 24 dispersed or contained in the second absorbent layer 18 should be in the range of from between about 5% to about 35%. Higher percentages of superabsorbents in the second absorbent layer 18 can disrupt the continuity of the fibrous portion of this layer and hence disrupt wicking throughout this layer. Preferably, the percentage of superabsorbent 24 contained in the second absorbent layer 18 will range from between about 8% to about 25%. Most preferably, the percentage of superabsorbent 24 contained in the second absorbent layer 18 will range from between about 10% to about 20%.

The absorbent article 10 also contains a baffle 26 located directly below the second absorbent layer 18. The baffle 26 should be liquid impermeable and should function to prevent the passage of body fluid out of the absorbent article 10. If desired, the baffle 26 can be constructed to allow or permit the passage of air and moisture vapor out of the absorbent article 10 while serving to block the passage of body fluid therefrom. The baffle 26 can cooperate with the liquid-permeable cover 12 to enclose the surge layer 14 and the absorbent core 20. Alternatively, the liquid-permeable cover 12 can wrap completely around the baffle 26 as well as the surge or transfer layer 14 and the absorbent core 20.

The baffle 26 can be an air permeable microporous film. Preferably, the baffle 26 is constructed from a thermoplastic film having a thickness of less than about 2 millimeters (mm). More preferably, the baffle 26 is constructed from a thermoplastic film having a thickness of less than about 1 mm. Examples of two thermoplastic film materials that work well as baffles are polyethylene and polypropylene. The material forming the baffle 26 can also be tinted or made of a special color, such as rose, blue, green or peach, to make the absorbent article 10 more attractive. Other materials from which the baffle 26 can be formed include foams. Polyolefin and polyurethane foams are two commonly used foams. Polyolefin foam can be made from either polyethylene or polypropylene. The baffle 26 can also be constructed from a liquid-permeable material that has been treated or coated to make it liquid impermeable.

Figure 3:
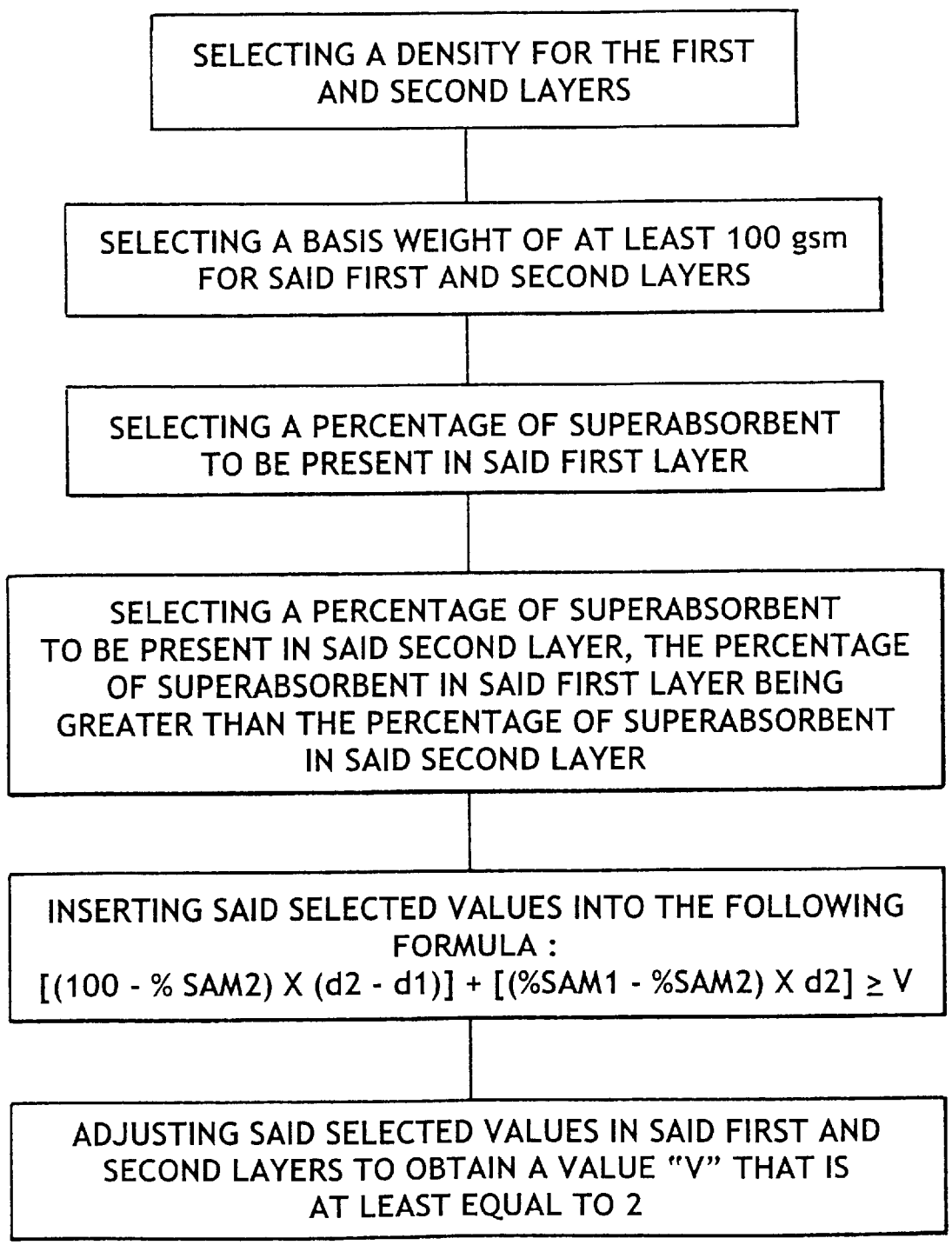
FIG. 3 is a flow diagram depicting a method of determining the efficiency of an absorbent article having two absorbent layers each having a selected density, basis weight and a desired percentage of a superabsorbent.

Referring now to FIG. 3, a flow diagram is depicted for the method of determining the efficiency of an absorbent article 10 having two absorbent layers, 16 and 18, each having a selected density, basis weight and each containing a desired percentage of a superabsorbent. By mathematically constructing an absorbent article 10 according to the following criteria, one can determine the efficiency of the absorbent article 10 before physically forming the article. This can reduce the amount of time needed to design a new absorbent article 10 and thereby make a manufacturer more productive and cost effective. Before using the method, one must have selected the material(s) that they desire to use in order to form the first and second absorbent layers, 16 and 18 respectively. Preferably, the first and second absorbent layers, 16 and 18 respectively, are formed from a wettable, fibrous material, such as cellulose fluff.

The method of determining the efficiency of the absorbent article 10 starts with the selection of a density for each of the first and second absorbent layers, 16 and 18 respectively. A basis weight is then selected for each of the first and second absorbent layers, 16 and 18 respectively. The basis weight for each absorbent layer 16 and 18 should be at least about 100 gsm. Preferably, the basis weight for each layer 16 and 18 is higher than 100 gsm and the preferred value is partially dictated by the type of article being produced, its overall size and the amount and kind of body fluid it is designed to absorb. The next item to be selected is the percentage of a superabsorbent to be present in the first absorbent layer 16. This percentage should range from between about 35% to about 80%. The percentage of a superabsorbent to be present in the second absorbent layer 18 is also selected. This percentage should range from between about 5% to about 35%. It should be noted that the percentage of a superabsorbent present in the first absorbent layer 16 is greater than the percentage of superabsorbent present in the second absorbent layer 18. This is an important feature of this invention.

The method further includes inserting the selected densities and percentages of superabsorbent into the following formula:

$$V \leq [(100 - \% \text{ SAM2}) \times (d2-d1)] + [(\% \text{ SAM1} - \% \text{ SAM2}) \times d2]$$

where: % SAM1 is the percentage of a superabsorbent present in said first absorbent layer;
% SAM2 is the percentage of a superabsorbent present in said second absorbent layer;
d1 is the density of said first absorbent layer expressed in gsm;
d2 is the density of said second absorbent layer expressed in gsm; and
V is the desired value to form an efficient absorbent article.

The selected densities and the selected percentages of a superabsorbent in each of the first and second absorbent layers are then adjusted to obtain a value "V" which is at least equal to 2. Preferably, the value "V" is greater than 4. More preferably the value "V" is greater than 6, and most preferably, the value "V" is from between about 6 and about 15. The higher the value "V", up to about 15, the more efficient the absorbent article 10 will be at absorbing body fluid.

It should be noted that the absorbent article 10 should be constructed such that unrestricted swelling of the superabsorbents 22 and 24 can physically occur. As the absorbent core 20 absorbs body fluid, the superabsorbents 22 and 24 present in the first and second absorbent layers, 16 and 18 respectively, will swell and grow in overall size. This will cause the first and second absorbent layers 16 and 18 to increase in height, width and length. The liquid-permeable cover 12 and/or the liquid impermeable baffle 26 should be designed to permit such enlargement of the absorbent core 20. An important aspect of this invention is to allow enough room between the cover 12 and the baffle 26 such that swelling can occur. If the cover 12 and/or the baffle 26 have the ability to expand or exhibit flexibility and/or stretch, they will not impede the swelling of the first and second absorbent layers, 16 and 18 respectively.

One way to assure that the enclosing perimeter "E" formed by the cover 12 and the baffle 26 is sufficient to allow swelling to occur is to size the cover 12 and the baffle 26 to account for this enlargement. The cross-sectional dimensions of the absorbent article 10 can be measured at its narrowest location and the dimensions of both the cover 12 and the baffle 26 surrounding this particular location can also measured. The enclosing perimeter "E" of a wet or insulted absorbent article 10 at the crotch location is equal to the length of the surrounding cover 12 and baffle 26. The enclosing perimeter "E" can be calculated according to the following formula:

$$E \geq 2 \times [((2 \times bw1 + bw2) \times f)^2 + wc]^2$$

where: bw1 is the basis weight of the first absorbent layer;
bw2 is the basis weight of the second absorbent layer;
f is a factor represented by the numerical number of 0.001, preferably 0.002, and most preferably, 0.0025; and
wc is the width of the first and second absorbent layers at the location where the enclosing perimeter "E" needs to be determined.

The unique two layer absorbent article 10 of this invention has a selected density, a selected basis weight and contains a desired percentage of a superabsorbent 22 and a superabsorbent 24 in each of the absorbent layers 16 and 18. An absorbent article 10 constructed according to the above teachings will exhibit rapid and preferential relocation of the incoming body fluid to the lower absorbent layer 18. The body fluid is directed away from the target area 28 of the cover 12, see FIG. 1, where a majority of the body fluid initially contacts the absorbent article 10. By moving the incoming body fluid down through the first absorbent layer 16 and into the lower absorbent layer 18, see FIG. 2, a void volume in the absorbent layer 16 is maintained beneath the cover 12. This feature allows additional incoming body fluid to be taken up by the absorbent article 10. It is believed that the effective capillary difference between the first and second absorbent layers, 16 and 18 respectively, is represented by the formula:

$$V \leq [(100 - \% \text{ SAM2}) \times (d2-d1)] + [(\% \text{ SAM1} - \% \text{ SAM2}) \times d2]$$

This capillary difference in combination with poor lateral connectivity of the fibrous portion of the first absorbent layer 16 leads to the body fluid rapidly moving down into the second absorbent layer 18. As the body fluid passes from the first absorbent layer 16 into the central portion of the second absorbent layer 18, it is quickly and readily directed downward and also outward in the longitudinal and transverse directions. The body fluid is transported away from the central location of second absorbent layer 18 and then is reabsorbed back into the first absorbent layer 16 for permanent retention. The absorbent capacity of the first absorbent layer 16 is higher than the absorbent capacity of the second absorbent layer 18 and this difference permits the body fluid to be retained by the first absorbent layer 16. The greater percentage of superabsorbent in the first absorbent layer 16 gives the first absorbent layer 16 its higher absorbent capacity.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A method of determining the efficiency of an absorbent article having first and second absorbent layers, said method comprising the steps of:
   a) selecting a density for said first and second absorbent layers;
   b) selecting a basis weight of at least about 100 gsm for each of said first and second absorbent layers;
   c) selecting a percentage of superabsorbent to be present in said first absorbent layer;
   d) selecting a percentage of superabsorbent to be present in said second absorbent layer, said percentage of superabsorbent present in said first absorbent layer being greater than said percentage of superabsorbent present in said second absorbent layer;
   e) inserting said selected densities and percentages of superabsorbent into the following formula:

$-V \leq [(100 \ldots V \leq [(100-\% \text{ SAM2}) \times (d2-d1)] + [(\% \text{ SAM1} - \% \text{ SAM2}) \times d2]$ where: % SAM1 is the percentage of a superabsorbent present in said first absorbent layer;
   % SAM2 is the percentage of a superabsorbent present in said second absorbent layer;
   d1 is the density of said first absorbent layer expressed in gsm;
   d2 is the density of said second absorbent layer expressed in gsm; and
   V is the desired value to form an efficient absorbent article; and
   f) adjusting said selected densities and said selected percentages of superabsorbent in said first and second absorbent layers to obtain a value "V" that is at least equal to 2.

2. The method of claim 1 further comprising selecting a density for said second absorbent layer that is less than said density of said first absorbent layer.

3. The method of claim 2 further comprising selecting a density for said second absorbent layer that is greater than said density of said first absorbent layer.

4. The method of claim 1 further comprising selecting a density for said first absorbent layer that is at least 0.08 grams per cubic centimeter (g/cc).

5. The method of claim 1 further comprising selecting a basis weight for said first absorbent layer that is at least about 150 grams per square meter.

6. The method of claim 1 further comprising selecting a basis weight for said second absorbent layer that is at least about 150 grams per square meter.

7. The method of claim 1 wherein said percentage of superabsorbent selected for said first absorbent layer is from between about 35% to about 80%.

8. The method of claim 1 wherein said percentage of superabsorbent selected for said second absorbent layer is from between about 5% to about 35%.

9. The method of claim 1 further comprising constructing said first absorbent layer from a wettable, fibrous material.

10. A method of determining the efficiency of an absorbent article having first and second absorbent layers, said method comprising the steps of:
    a) selecting a wettable, fibrous material from which to form said first and second absorbent layers;
    b) selecting a density for said first and second absorbent layers;
    c) selecting a basis weight of at least about 100 gsm for each of said first and second absorbent layers;
    d) selecting a percentage of superabsorbent to be present in said first absorbent layer;
    e) selecting a percentage of superabsorbent to be present in said second absorbent layer, said percentage of superabsorbent present in said first absorbent layer being greater than said percentage of superabsorbent present in said second absorbent layer;
    f) inserting said selected densities and percentages of superabsorbent into the following formula:

$V \leq [(100-\% \text{ SAM2}) \times (d2-d1)] + [(\% \text{ SAM1} - \% \text{ SAM2}) \times d2]$ where: % SAM1 is the percentage of a superabsorbent present in said first absorbent layer,
    % SAM2 is the percentage of a superabsorbent present in said second absorbent layer,
    d1 is the density of said first absorbent layer expressed in gsm;
    d2 is the density of said second absorbent layer expressed in gsm; and
    V is the desired value to form an efficient absorbent article; and
    g) adjusting said selected densities and said selected percentages of superabsorbent in said first and second absorbent layers to obtain a value "V" that is at least equal to 4.

11. The method of claim 10 further comprising selecting a basis weight for said first absorbent layer that is at least about 150 grams per square meter.

12. The method of claim 10 further comprising selecting a basis weight for said second absorbent layer that is at least about 150 grams per square meter.

13. The method of claim 10 further comprising selecting a density for said first absorbent layer that is from between about 0.08 g/cc to about 0.18 g/cc.

14. The method of claim 10 further comprising selecting a density for said second absorbent layer that is from between about 0.1 g/cc to about 0.2 g/cc.

15. A method of determining the efficiency of an absorbent article having first and second absorbent layers, said method comprising the steps of:
    a) selecting a density for said first and second absorbent layers;
    b) selecting a basis weight of at least about 100 gsm for each of said first and second absorbent layers;

c) selecting a percentage of superabsorbent to be present in said first absorbent layer;

d) selecting a percentage of superabsorbent to be present in said second absorbent layer, said percentage of superabsorbent present in said first absorbent layer being greater than said percentage of superabsorbent present in said second absorbent layer;

e) inserting said selected densities and percentages of superabsorbent into the following formula:

$$V \leq [(100 - \% \text{ SAM2}) \times (d2 - d1)] + [(\% \text{ SAM1} - \% \text{ SAM2}) \times d2]$$

where: % SAM1 is the percentage of a superabsorbent present in said first absorbent layer, % SAM2 is the percentage of a superabsorbent present in said second absorbent layer, d1 is the density of said first absorbent layer expressed in gsm;

d2 is the density of said second absorbent layer expressed in gsm; and

V is the desired value to form an efficient absorbent article; and f) adjusting said selected densities and said selected percentages of superabsorbent in said first and second absorbent layers to obtain a value "V" that is at least equal to 6.

16. The method of claim 15 further comprising adjusting said selected densities and said selected percentages of a superabsorbent in said first and second absorbent layers to obtain a value of from between about 6 to about 15.

17. The method of claim 15 further comprising selecting a wettable, fibrous material from which to form said first and second absorbent layers.

18. The method of claim 15 further comprising selecting a density for said first absorbent layer which is from between about 0.08 g/cc to about 0.18 g/cc and selecting a percentage of a superabsorbent in said first absorbent layer which is from between about 35% to about 80%.

19. The method of claim 15 further comprising selecting a density for said second absorbent layer which is from between about 0.1 g/cc to about 0.2 g/cc and selecting a percentage of a superabsorbent in said second absorbent layer which is from between about 5% to about 35%.

20. The method of claim 15 further comprising sizing said cover and baffle to have an enclosing perimeter "E" which is calculated by the formula:

$$E \geq 2 \times [((2 \times bw1 + bw2) \times f)^2 + wc]^2$$

where: bw1 is the basis weight of the first absorbent layer;

bw2 is the basis weight of the second absorbent layer;

f is a factor represented by the numerical number of 0.001, preferably 0.002, and most preferably, 0.0025; and wc is the width of the first and second absorbent layers at the location where the enclosing perimeter "E" needs to be determined.

* * * * *